(12) United States Patent
Cheng et al.

(10) Patent No.: US 8,361,084 B2
(45) Date of Patent: Jan. 29, 2013

(54) MEDICAL RETRIEVAL BASKETS

(75) Inventors: Eric Cheng, Bloomington, IN (US);
Norman Dillinger, Ellettsville, IN (US);
James A. Teague, Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 581 days.

(21) Appl. No.: 11/892,563

(22) Filed: Aug. 23, 2007

(65) Prior Publication Data

US 2008/0058834 A1 Mar. 6, 2008

Related U.S. Application Data

(60) Provisional application No. 60/841,516, filed on Sep. 1, 2006.

(51) Int. Cl.
*A61B 17/22* (2006.01)
(52) U.S. Cl. ........................................... 606/127
(58) Field of Classification Search .................. 606/110, 606/113–114, 127–128, 167, 170, 180; 600/101, 600/104, 106, 137
See application file for complete search history.

(56) References Cited

U.S. PATENT DOCUMENTS

| 5,100,423 | A * | 3/1992 | Fearnot | 606/159 |
| 6,168,603 | B1 * | 1/2001 | Leslie et al. | 606/114 |
| 6,190,394 | B1 * | 2/2001 | Lind et al. | 606/127 |
| 6,224,612 | B1 | 5/2001 | Bates et al. | |
| 6,348,056 | B1 | 2/2002 | Bates et al. | |
| 6,383,196 | B1 | 5/2002 | Leslie et al. | |
| 6,893,450 | B2 | 5/2005 | Foster | |
| 6,942,673 | B2 | 9/2005 | Bates et al. | |
| 2001/0041899 | A1 | 11/2001 | Foster | |
| 2002/0010487 | A1 * | 1/2002 | Evans et al. | 606/180 |

FOREIGN PATENT DOCUMENTS

| DE | 197 22 429 A1 | 12/1998 |
| WO | WO 96/23446 | 8/1996 |
| WO | WO 01/97699 A1 | 12/2001 |

OTHER PUBLICATIONS

Annex to Form PCT/ISA/206 dated Jan. 7, 2008, issued in corresponding International Application No. PCT/US2007/077089 (2 pages).

* cited by examiner

*Primary Examiner* — Ryan Severson
*Assistant Examiner* — Ashley Cronin
(74) *Attorney, Agent, or Firm* — Bookoff McAndrews, PLLC

(57) ABSTRACT

A medical retrieval device includes a basket formed of two or more legs. The basket may be used to retrieve material (e.g., a urinary stone) from a body. The basket opens and closes for encapsulation of a stone. A captured stone may be released from the basket with the basket still in the body by opening the legs. The baskets exhibit shapes and configurations designed to optimize the characteristics of flexibility, ease of material capture, and ease of material release.

29 Claims, 7 Drawing Sheets

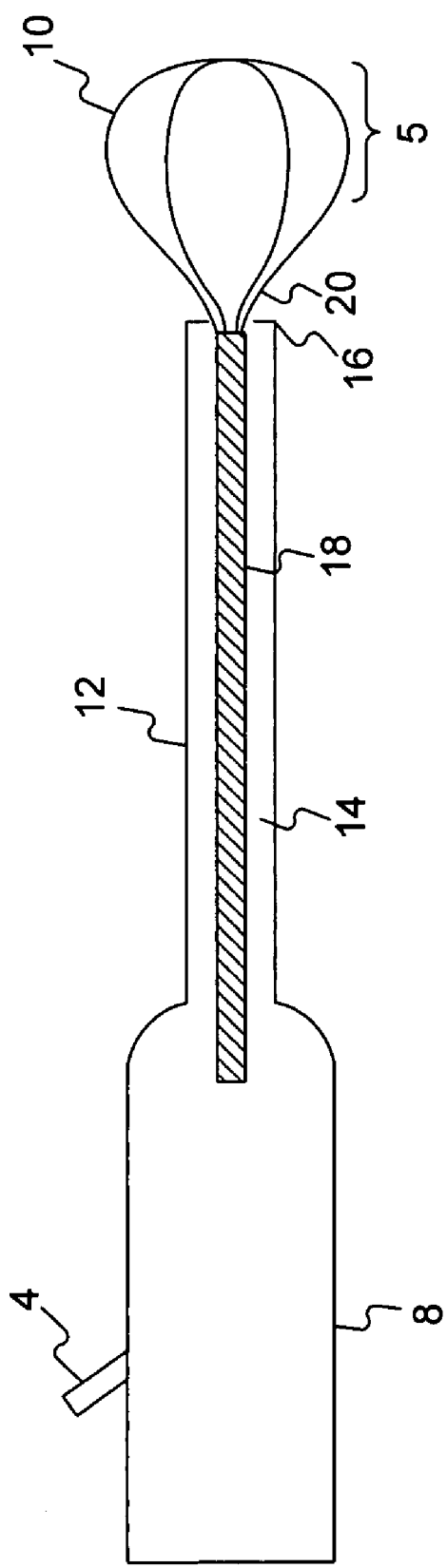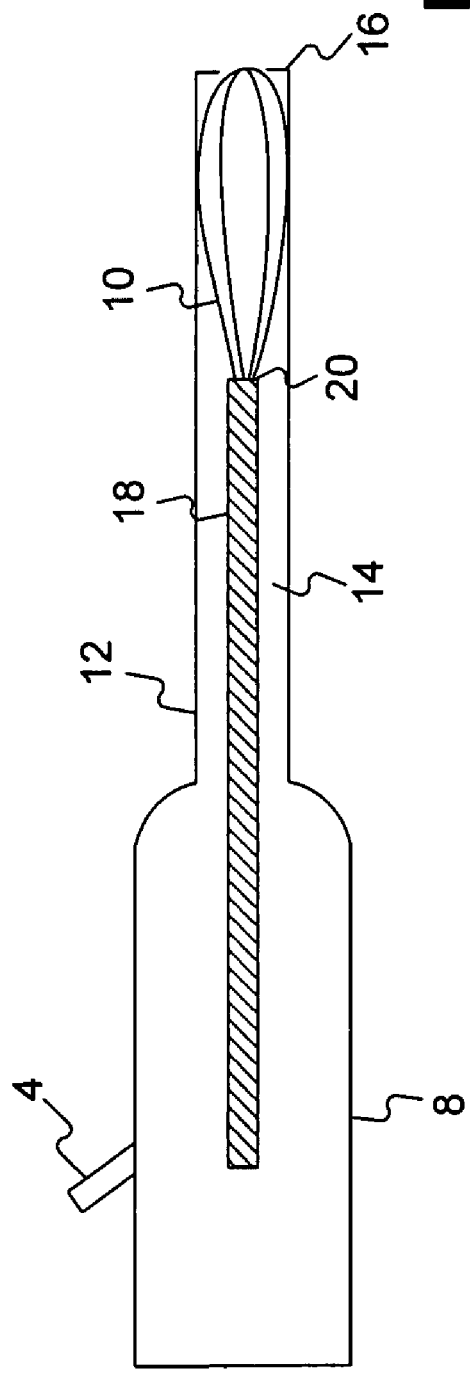

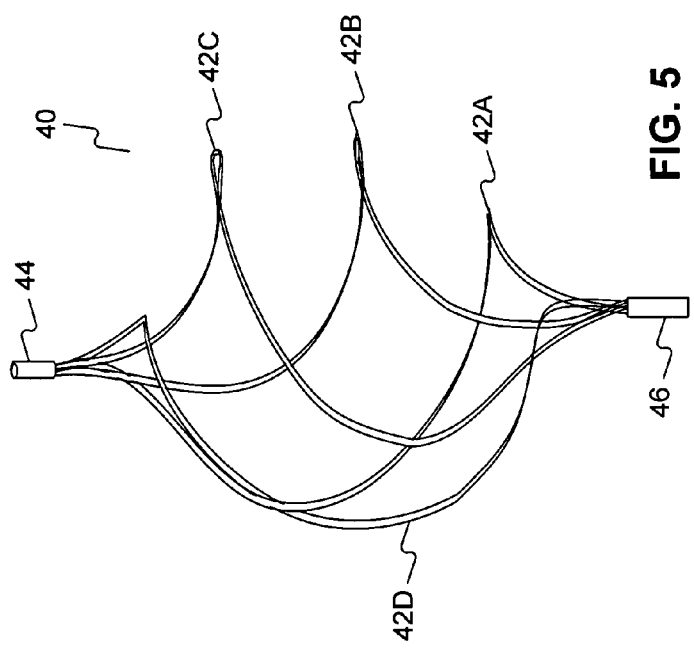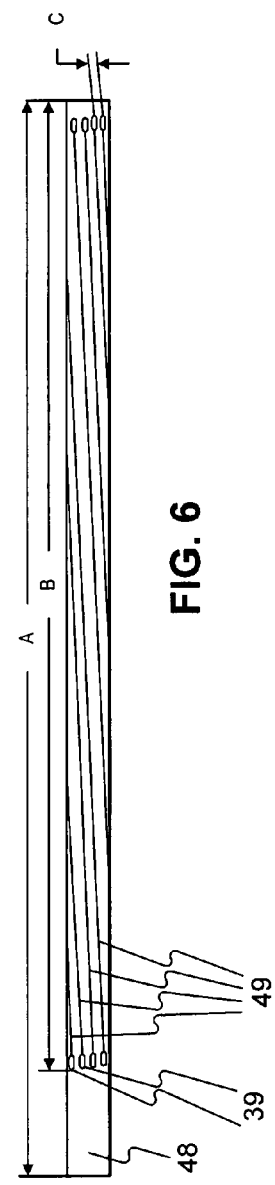

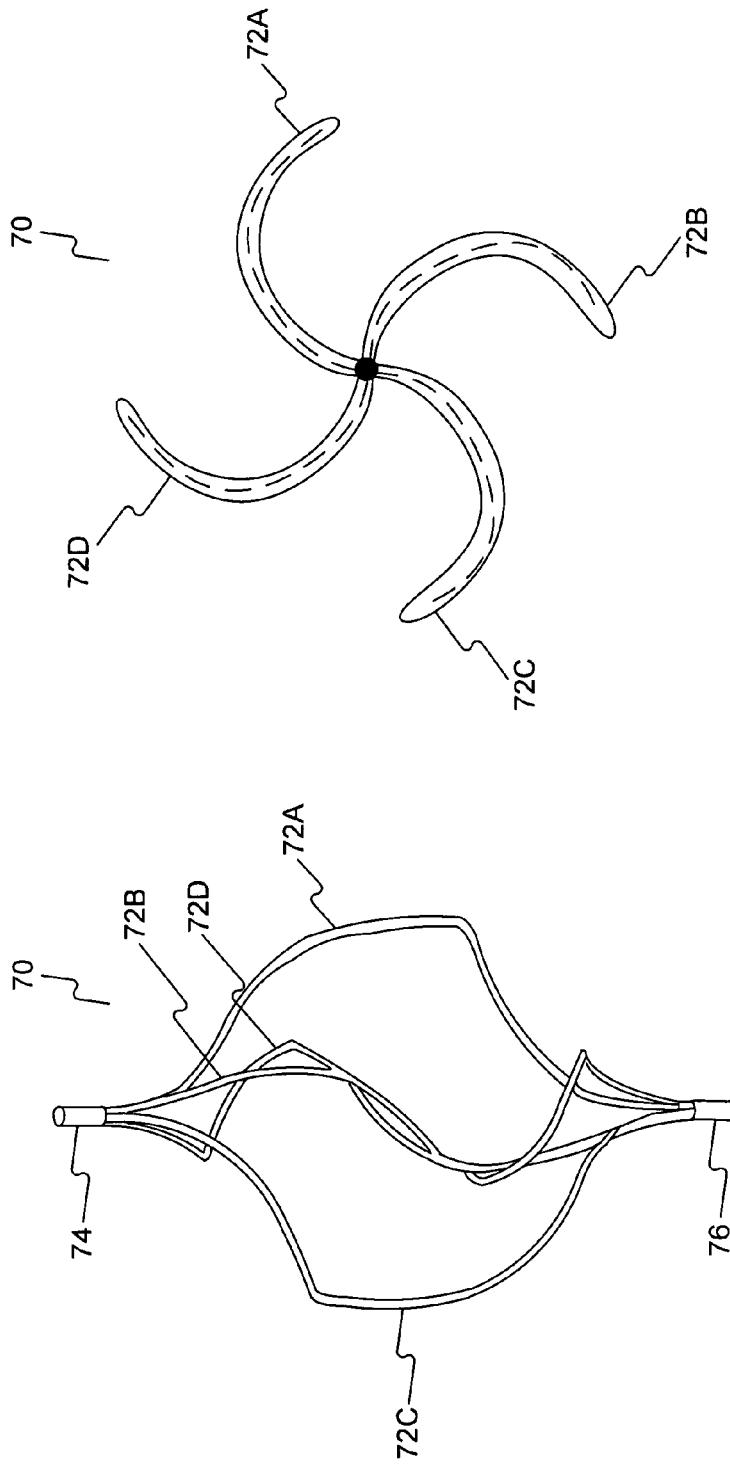

MEDICAL RETRIEVAL BASKETS

CROSS-REFERENCE TO RELATED APPLICATIONS

This application claims the priority of earlier filed U.S. Provisional Application No. 60/841,516, filed Sep. 1, 2006. The entire content of that provisional application is expressly incorporated by reference herein.

FIELD OF THE INVENTION

The invention relates generally to medical devices for retrieving material from within a body. More particularly, embodiments of the invention relate to medical retrieval baskets intended to be used endoscopically to grasp, manipulate, and remove material from the urinary tract. The medical retrieval devices exhibit shapes and configurations designed to optimize the characteristics of, for example, flexibility, ease of material capture, and ease of material release.

BACKGROUND OF THE INVENTION

Medical retrieval devices may include devices for removing organic material (e.g., blood clots, tissue, and biological concretions such as urinary, biliary, and pancreatic stones) and inorganic material (e.g., components of a medical device or other foreign matter), which may obstruct or otherwise be present within a body's anatomical lumens. For example, concretions can develop in certain parts of the body, such as in the kidneys, pancreas, and gallbladder. Minimally invasive medical procedures generally involve causing limited trauma to the tissues of a patient, and can be used to dispose of problematic concretions. Lithotripsy and ureteroscopy, for example, are used to treat urinary calculi (e.g., kidney stones) in the ureter of a patient.

Lithotripsy is a medical procedure that uses energy in various forms such as acoustic shock waves, pneumatic pulsation, electrical hydraulic shock waves, or laser beams to break up biological concretions such as urinary calculi (e.g., kidney stones). The force of the energy, when applied either extracorporeally or intracorporeally, usually in focused and continuous or successive bursts, divides a kidney stone into smaller fragments that may be extracted from the body or allowed to pass through urination.

When stones are fragmented within a body tract by a lithotripter, the stone must first be stabilized. Typically, a medical retrieval device, such as a surgical grasper or a metal wire basket, is used to capture a stone in the retrieval assembly. With the stone held in position within the retrieval assembly, a lithotripter, such as a laser lithotriptor, comes into proximity with the stone and the stone is fragmented by the lithotriptor. After the stone is fragmented, the stone fragments can be removed by the same or a different medical retrieval device, or the fragments can be left in the body to be eliminated naturally. With the help of imaging tools such as transureteroscopic video technology and fluoroscopic imaging, the operator of the lithotriptor device can monitor the progress of the medical procedure and terminate treatment when residual fragments are small enough to be voided or removed with minimal trauma.

Retrieval of intracorporeal fragments of urinary calculi can be problematic in that stones and/or stone fragments in the ureter often migrate within the body before, during, and after a lithotripsy procedure. Therefore, a need exists in the art for a retrieval device that facilitates the initial capture of material as well as maintaining capture of material during further positioning and removal of the captured material and retrieval device. In addition, there also exists a need in the art for a retrieval device that facilitates the controlled release of a stone or fragment during a surgical procedure. For example, controlled release of material is often required to reposition a target stone relative to a lithotriptor or release a captured stone of a size too large for removal without fragmentation.

Thus, it is desirable to have configurations for medical retrieval devices that exhibit improved capabilities for sustained capture, controlled release, and limited patient tissue trauma.

SUMMARY OF THE INVENTION

Embodiments of the present invention are directed to medical devices for retrieval of objects within anatomical lumens of the body that obviate one or more of the limitations and disadvantages of prior retrieval devices.

In one embodiment, the medical device includes a sheath having a proximal end and a distal end and a basket for removing material from a body. The basket has a distal end, a proximal end, a longitudinal axis, a collapsed position where the basket is enclosed within the sheath, and an expanded position where the basket extends from the distal end of the sheath. The basket includes at least two struts each comprised of two legs united in a paired configuration, the struts twisting in a spiral configuration about the longitudinal axis of the basket.

In various embodiments, the medical device may include one or more of the following additional features: wherein the basket includes a distal basket portion and a proximal basket portion, the distal basket portion including at least three struts, and wherein the struts of the distal basket portion merge to form two struts in the proximal basket portion; wherein each of the two struts of the proximal basket portion is wider than each of the at least three struts of the distal basket portion; wherein the two legs of each strut are united with each other along their entire lengths; wherein the struts of the distal basket portion merge at a basket point midway between the distal and proximal ends of the basket; wherein the basket is formed by cuts made in a hollow tube; wherein the two legs of each strut are comprised of a shape memory material and exhibit substantially identical complementary shapes; wherein the two legs of each strut are united at a single point between their respective distal and proximal ends; wherein the two legs of each strut are united at multiple points along their lengths; wherein the two legs of each strut are united only at their distal and proximal ends; wherein the two legs of each strut are united through welds, solder, or adhesives; and wherein the legs are comprised of individual metal wires.

Another embodiment of the invention is directed to a medical device including a sheath having a proximal end and a distal end and a basket for removing material from a body. The basket has a distal end, a proximal end, a longitudinal axis, a collapsed position where the basket is enclosed within the sheath, an expanded position where the basket extends from the distal end of the sheath, and at least two legs extending between the distal and proximal basket ends. Each of the legs twists in a spiral configuration about the longitudinal axis of the basket. The basket includes a distal basket portion and a proximal basket portion and wherein the distal basket portion includes at least three legs that merge to form two legs in the proximal basket portion.

In various embodiments, the medical device may include one or more of the following additional features: wherein each of the two legs of the proximal basket portion is wider than each of the at least three legs of the distal basket portion;

wherein the at least three legs of the distal basket portion merge at a basket point midway between the distal and proximal ends of the basket; wherein the basket is formed through cuts made in a hollow tube; and wherein all the legs are comprised of individual metal wires.

Another embodiment of the invention is directed to a medical device including a sheath having a proximal end and a distal end and a basket for removing material from a body. The basket has a distal end, a proximal end, a longitudinal axis, a collapsed position where the basket is enclosed within the sheath, and an expanded position where the basket extends from the distal end of the sheath. The basket includes at least one leg having a first portion twisting in a first spiral direction about the longitudinal axis and a second portion twisting in a second spiral direction about the longitudinal axis, the second spiral direction being opposite of the first spiral direction.

In various embodiments, the medical device may include one or more of the following additional features: wherein the first spiral direction is clockwise and the second spiral direction is counter-clockwise; wherein the at least one leg includes a third portion twisting in a first spiral direction about the longitudinal axis, the second portion being between the first and third portions; wherein the at least one leg includes four legs; wherein the basket includes a distal basket portion and a proximal basket portion, the distal basket portion including at least three legs and wherein the legs of the distal basket portion merge to form two legs in the proximal basket portion; wherein each of the two legs of the proximal basket portion is wider than each of the at least three legs of the distal basket portion; wherein the at least one leg is an individual metal wire; wherein the at least three legs of the distal basket portion merge at a basket point midway between the distal and proximal ends of the basket; wherein the basket is formed through cuts made in a hollow tube; and wherein the cuts form a herringbone pattern.

Another embodiment of the invention is directed to a method of forming a medical retrieval basket including providing a hollow tube having a longitudinal axis and forming a herringbone pattern of separate slots in the tube such that the material of the tube remaining between the slots forms legs of the basket. In addition, each slot is angled relative to the longitudinal axis.

In various embodiments, the method may include one or more of the following additional features: wherein each of the separate slots extends at a first angle relative to the longitudinal axis of the tube and changes direction to extend at a second angle relative to the longitudinal axis of the tube; wherein each slot changes direction at a common position along the length of the tube; and wherein the angles formed by each of the slots are the same; wherein the angles formed by each of the slots are different; and providing a sheath configured to receive the basket and providing a handle at the proximal end of the sheath.

Another embodiment of the invention is directed to a method of forming a medical retrieval basket including providing a hollow tube having a longitudinal axis and forming a pattern of slots in the tube parallel to the longitudinal axis such that the material of the tube remaining between the slots forms legs of the basket. At least two slots are longer than the remaining slots.

In various embodiments, the method may include the following additional features: providing a sheath configured to receive the basket and providing a handle at the proximal end of the sheath; and wherein a proximal portion of each of the at least two slots is wider than the remaining slots.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1 illustrates a medical retrieval device with a retrieval basket according to the present disclosure, with the basket in an expanded position.

FIG. 2 illustrates a medical retrieval device with a retrieval basket according to the present disclosure, with the basket in a collapsed position.

FIG. 5 is a perspective view of a medical retrieval basket, according to another embodiment of the present disclosure.

FIG. 6 depicts a flat rendition of a tube cut to form the medical retrieval basket of FIG. 5, according to an embodiment of the present disclosure.

FIG. 10 illustrates a perspective view of a medical retrieval basket depicting a herringbone shaped configuration, according to an embodiment of the present disclosure.

FIG. 11 illustrates a top view of the medical retrieval basket of FIG. 10, according to an embodiment of the present disclosure.

FIG. 12 depicts a flat rendition of a tube cut to form the medical retrieval basket of FIG. 10, according to an embodiment of the present disclosure.

DESCRIPTION OF THE EMBODIMENTS

Figure 3:
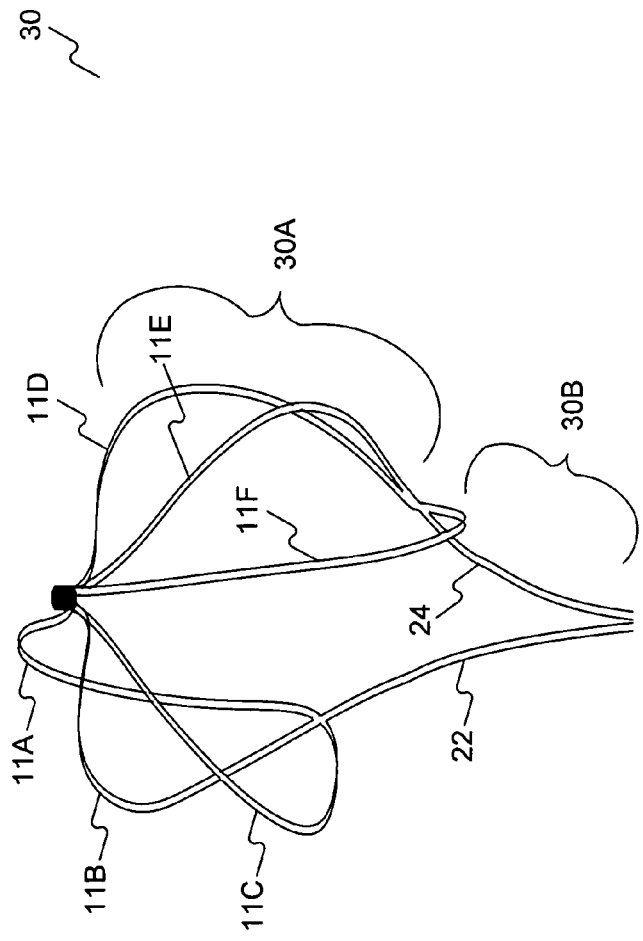
FIG. 3 is a perspective view of a medical retrieval basket, according to an embodiment of the present disclosure.

Reference will now be made in detail to the present exemplary embodiments of the invention illustrated in the accompanying drawings. Wherever possible, the same reference numbers will be used throughout the drawings to refer to the same or like parts. The drawing figures of this application are intended to provide a general understanding of the working elements of the underlying device. Accordingly, unless explicitly stated, the figures do not represent a literal depiction of proportional dimensions or the precise locations for the illustrated inter-related components.

Embodiments of the invention include a basket of a medical retrieval device having at least two basket legs. FIGS. 1 and 2 show an exemplary basket 10 in expanded and collapsed positions, respectively, relative to a sheath 12. For purposes of this disclosure, "distal" refers to the end further from the device operator during use and "proximal" refers to the end closer to the device operator during use.

The basket 10, shown by way of example in FIG. 1, is the type that can be collapsed within sheath 12 for entry into the body. A medical retrieval device that includes the basket 10 also includes the sheath 12 and a proximal handle 8. The handle 8, sheath 12, and basket 10 illustrated in FIGS. 1 and 2 are not shown in their correct size or proportion to each other. The size of the entire sheath 12 is dimensioned to fit the requirements of its application in the body. For example, for urological applications, the size of the device is typically 1.7-8.0 French in diameter and approximately 75-135 cm in length. It is contemplated, however, that other dimensions would be appropriate depending on the patient and particular treatment desired. The sheath 12 has at least one lumen 14 therein, may be made from a single material, and extends from the handle 8 to a distal sheath end 16. An elongated member such as a cable, coil, shaft, guidewire, or mandril wire 18 extends within the lumen 14 from an actuating mechanism 4 at the device handle 8 to the base 20 of the basket 10, where the cable 18 is attached to the basket base 20. Operation of the actuating mechanism 4 by an operator causes the basket 10 to move in and out of the sheath 12 between a collapsed position within the sheath 12 as illustrated in FIG. 2 to an extended position outside of the sheath 12 where the basket 10 is open/expanded and extending beyond the distal end of the sheath 16 as shown in FIG. 1.

Alternatively, the mechanism 4 can cause movement of the sheath 12 to advance the sheath 12 over the stationary basket 10 and cable 18 combination, to thereby collapse the basket 10 within the sheath 12. The mechanism 4 can slide the moveable sheath 12 back to expose the stationary basket 10 and allow it to open/expand.

With the basket collapsed within the sheath 12 as shown in FIG. 2, the sheath 12 can be inserted into the body by an operator to a site in the body where the material to be retrieved is located (e.g., a stone in the ureter). By putting the basket 10 into its open/expanded position, as illustrated in FIG. 1, the basket 10 can be manipulated by the operator to entrap or capture material within the basket 10. The basket 10 and/or the sheath 12 can then be moved to cause the legs 11 of the basket 10 to close around the material and capture it. The captured material is then withdrawn from the body along with the sheath 12 and the basket 10 that is holding the material.

Medical retrieval devices can be formed to have baskets that are constructed by joining multiple legs together at a base of the basket and at a distal end or tip of the basket such that a "cage" is formed. In accordance with embodiments of the present disclosure, a method of basket formation involves starting with a hollow tube or cannula. For vertical basket features (i.e. features extending substantially axially along the longitudinal axis of the underlying basket structure) slots are cut lengthwise along the exterior of the cannula wall substantially parallel to the longitudinal axis of the cannula. For helical, spiral, or other non-vertical features, diagonal slots are cut with both an axial and a radial component. After cutting and cleaning, the resulting tubes are compressed lengthwise to spread the legs and manipulate the legs into a desired shape. This shape is then annealed into the material to form a desired basket configuration. The slotting pattern can be formed according to a laser cutting process. Other machining processes are possible, such as chemical etching and EDM (Electrical Discharge Machining).

The basket configuration according to embodiments of the present disclosure can be made at least partially of a shape-memory material. Shape-memory material is a material that can be formed into a particular shape, retain that shape during resting conditions (e.g., when the shaped material is in free space or when external forces applied to the shaped material are insufficient to substantially deform the shape), be deformed into a second shape when subjected to a sufficiently strong external force, and revert substantially back to the initial shape when external forces are no longer applied. Examples of shape memory materials include synthetic plastics, stainless steel, and superelastic, metallic alloys of nickel/titanium (e.g., Nitinol), copper, cobalt, vanadium, chromium, iron, or the like. Alternative basket materials include, but are not limited to, other metal alloys, powdered metals, ceramics, thermal plastic composites, ceramic composites, and polymers. Also, combinations of these and other materials can be used.

FIG. 3 depicts a perspective view of a medical retrieval basket according to an embodiment of the present disclosure. In FIG. 3, medical retrieval basket 30 consists of a distal primary basket portion 30A and a proximal secondary basket portion 30B. The primary basket portion 30A is comprised of six legs 11A-11F. At about the mid-point of the basket 30 (i.e. the half extended position of basket 30), legs 11A-11C merge into a first root leg 22. Similarly, legs 11D-11F merge at about the mid-point of the basket 30 into a second root leg 24. Legs 11A-11C and Legs 11D-11F may merge at alternative locations other than the mid-point of the basket 30. The particular merge point can be selected depending on the desired size between the partially opened basket in a "capture mode" and a fully opened basket in a "release mode." For example, the merge point may be ⅓ the length of the basket or ⅔ the length of the basket (further alternative merge point locations are contemplated).

First and second root legs 22 and 24 themselves merge at the base 20 of the basket 30, where connection can be made to a cable, for example, for controlled deployment and retraction of the basket 30 during a retrieval procedure. Alternatively, legs 22, 24 can merge into a proximal portion of the cannula from which the basket 30 is formed, and that proximal portion of the cannula can extend through the device to the handle for controlled deployment and retraction of basket 30.

During a retrieval procedure, the shape of basket 30 can facilitate the release of material captured within the primary basket portion 30A. For example, captured material can be released by an operator through controlled continued extension of the proximal secondary basket portion 30B relative to a housing sheath, such as, for example, sheath 12 depicted in FIG. 1 and FIG. 2. Release of captured material can be achieved by deploying the basket 30 to a fully expanded position. In such a position, the extension of root legs 22 and 24 from the sheath distal end results in a deployed basket configuration exhibiting an exposed void which provides an enlarged release path for discharge of material.

While a six leg configuration is illustrated for the primary basket portion 30A, other configurations are contemplated. Alternative configurations for basket 30 include, but are not limited to, four and eight leg primary basket configurations merging into a two legged secondary basket portion 30B.

Figure 4:
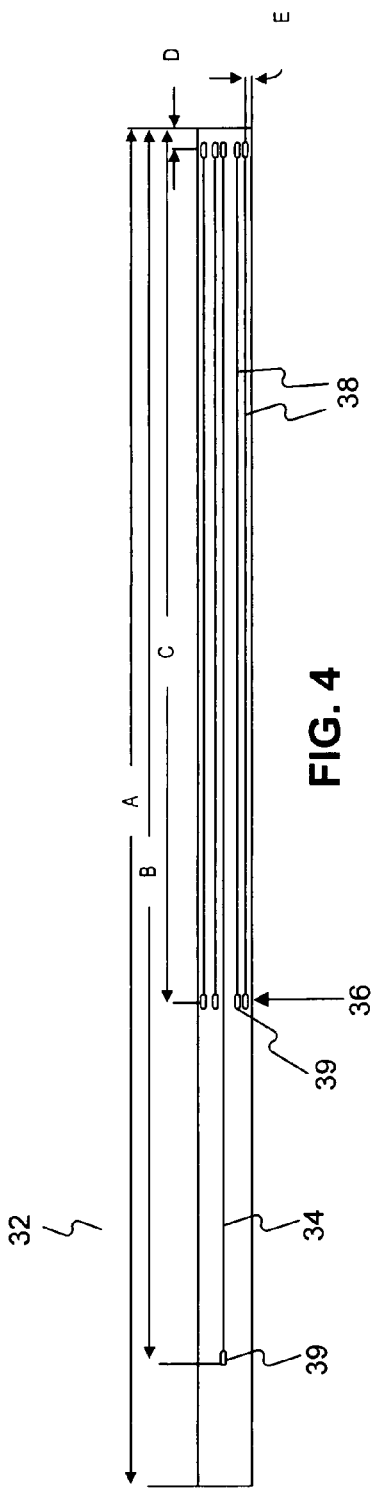
FIG. 4 depicts a flat rendition of a tube cut to form the medical retrieval basket of FIG. 3, according to an embodiment of the present disclosure.

FIG. 4 depicts a flat rendition of a tube 32 cut to form the medical retrieval basket of FIG. 3, according to an embodiment of the present disclosure. In other words, tube 32, in this view, has been unrolled and flattened to depict the cuts made to form the basket 30. The extended slot 34 originating on the left side of tube 32 separates a proximal portion of tube 32 into the two root legs 22 and 24 as depicted in FIG. 3. At the position where legs 11A-11F merge to form root legs 22 and 24, marked by arrow 36, additional relatively short slots 38 are cut in tube 32. The slots 38 form the spaces between the legs 11A-11F of FIG. 3. Accordingly, the number of slots 38 can be increased or decreased depending on the number of legs desired for the primary basket portion 30A of FIG. 3.

While the dimensions of tube 32, slots 34, and slots 38 can be altered depending on the particular application, exemplary non-limiting dimensions for the distances designated as A-E in FIG. 4 are as follows: A=1.293 inches; B=1.175 inches; C=0.8310 inches; D=0.020 inches; E=0.0068 inches. In addition, an exemplary non-limiting distance between slots 38 (i.e. the width of a basket leg 11) is about 0.0074 inches. In order to prevent the propagation of slots 34 and 38 beyond their predetermined lengths, stress relief features 39 can be formed at the terminal portions of slots 34 and 38. In the illustrated embodiment of FIG. 4, for example, stress relief features 39 are formed of enlarged openings that serve to prevent formation and/or propagation of a tear or rupture in tube 32 along slots 34 and 38.

FIG. 5 depicts a helical medical retrieval basket 40. Basket 40 is comprised of four legs 42A-42D joined together at a distal end 44 and a proximal end 46 of basket 42. As seen in FIG. 5, each leg 42A-42D is formed in a spiral configuration. As noted above, for helical, spiral, or other non-vertical leg configurations, slots are cut into a tube having both an axial and a radial component. For example, legs 42A-42D can be formed through continuous diagonal slots cut into a tube, thereby causing the individual legs 42A-42D to twist in a spiral configuration about the longitudinal axis of the basket 40. Such a spiral shape may be preferred by some physicians, for improved capturing of multiple small stones.

FIG. 6 depicts a flat rendition of a tube 48 cut to form the medical retrieval basket of FIG. 5, according to an embodiment of the present disclosure. Tube 48 includes four diagonal slots 49 extending around the exterior circumference of the tube. The slots 49 form the spaces between the legs 42A-42D of FIG. 5. Accordingly, the number of slots 49 can be increased or decreased depending on the number of legs desired for basket 40 of FIG. 5. Slots 49 can also be provided in various alternative arrangements resulting in shape changes for the underlying basket 40. For example, the pitch, or angle, of slots 49 can be increased or decreased, thereby altering the shape of the helical basket structure.

While the dimensions of tube 48 and slots 49 can be altered depending on the particular application, exemplary non-limiting dimensions for the distances designated as A-C in FIG. 6 are as follows: A=1.19 inches; B=1.07 inches; and C=0.0133 inches. Just as in the embodiment of FIG. 4, tube 48 of FIG. 6 includes stress relief features 39 formed at the terminal portions of slots 49. In the illustrated embodiment of FIG. 4, for example, stress relief features 39 are formed of enlarged openings that serve to prevent formation and/or propagation of a tear or rupture in tube 32 along slots 34 and 38.

Figure 7:
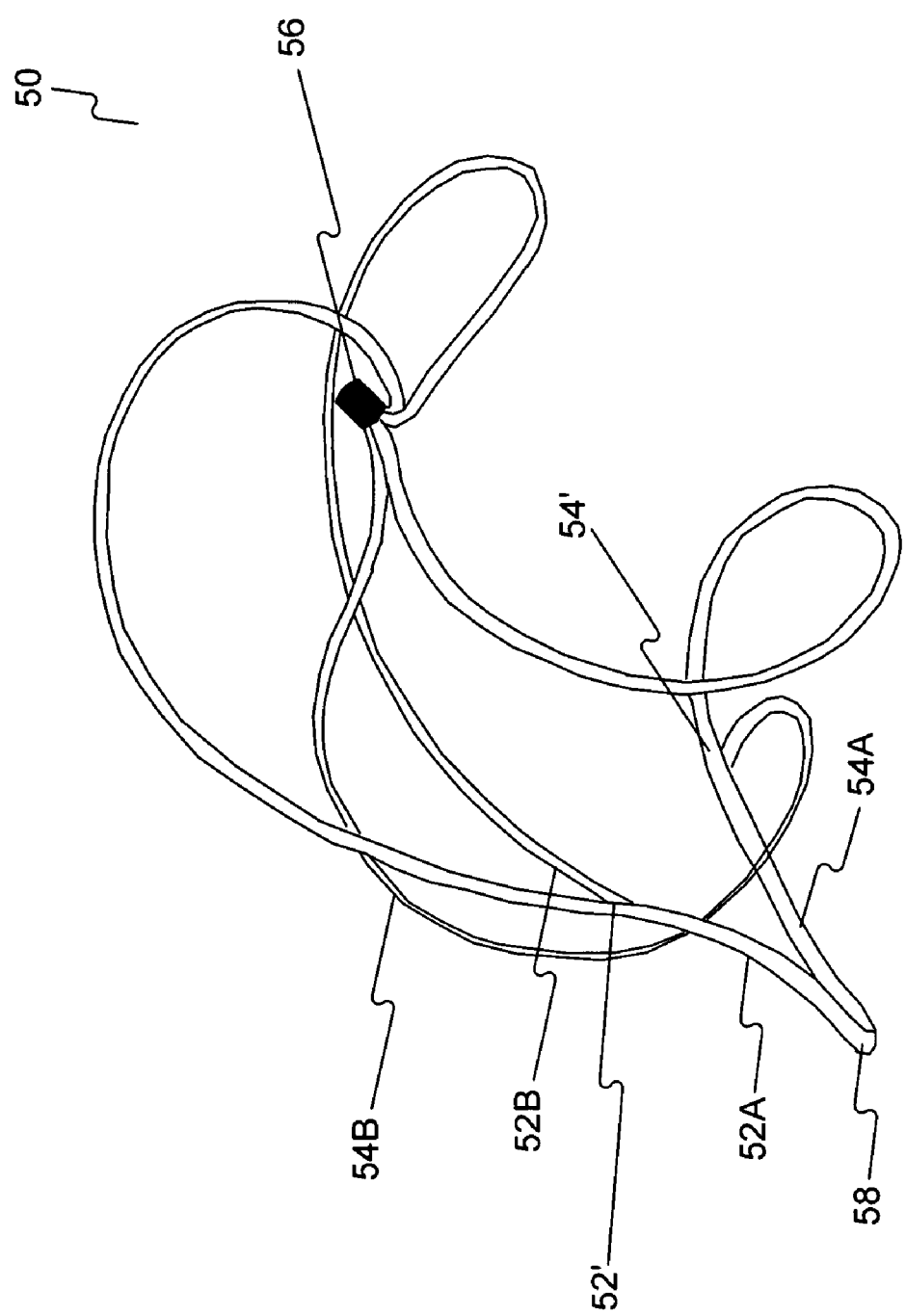
FIG. 7 is a perspective view of a medical retrieval basket, according to another embodiment of the present disclosure.

FIG. 7 depicts a perspective view of a medical retrieval basket according to another embodiment of the present disclosure. In FIG. 7, medical retrieval basket 50 depicts a combination of the merged leg feature of basket 30 and the spiral leg feature of basket 40. Accordingly, retrieval basket 50 includes a four leg configuration comprising root legs 52A and 54A and secondary branch legs 52B and 54B. As seen in FIG. 7, each of legs 52A-52B and 54A-54B extend from a distal end 56 and twist in a spiral configuration about the longitudinal axis of the basket 50. At an intermediate point 52' of leg 52A, leg 52B merges with leg 52A. Similarly, leg 54B merges with leg 54A at an intermediate point 54' along leg 54A. Legs 52A and 54A themselves merge at the base 58 of the basket 50, where connection can be made to a cable, for example, for controlled deployment and retraction of the basket 50 during a retrieval procedure.

Basket 50 of FIG. 7 can be formed by modifying the slotting pattern illustrated in FIG. 6. For example, in order to form the root legs 52A and 54A, two of the slots 49 of FIG. 6 will be lengthened relative to the remaining slots 49. In addition, the tube from which the basket 50 is formed can include diagonal slots extending around the exterior circumference of the tube until the intended point for merging the legs. In one formation, after the leg merging point, the slots then extend vertically (i.e. parallel to the left right direction (or long axis of tube 48) as viewed in FIG. 6, for example) as opposed to the diagonal direction. This configuration may be helpful in creating a clearer opening between legs for facilitating stone release.

Just as in the embodiment of FIG. 3, during a retrieval procedure, the shape of basket 50 can facilitate the controlled release of material captured within the basket. For example, material captured within the four legged helical basket 50 can be released by an operator through controlled continued extension of the proximal basket portion formed only of merged legs 52A and 54A relative to a housing sheath. Release of captured material can be achieved by deploying the basket 50 to a fully expanded position.

The extension of the proximal portion of legs 52A and 54A from a distal end of a sheath results in a deployed basket configuration having the benefits of (1) a spiral leg configuration and (2) an enlarged exposed void that provides an enlarged release path for discharge of material. Accordingly, the helical and merged leg release features can be used together to form a basket with legs that separate, upon continued expansion, to form a basket with long legs that separate the underlying spiral shape for stone release.

While a four leg configuration is illustrated for the distal portion of basket 50, other configurations are contemplated. Alternative configurations for basket 50 include, but are not limited to, four and eight leg distal basket configurations merging into a two legged proximal basket portion.

Figure 9:
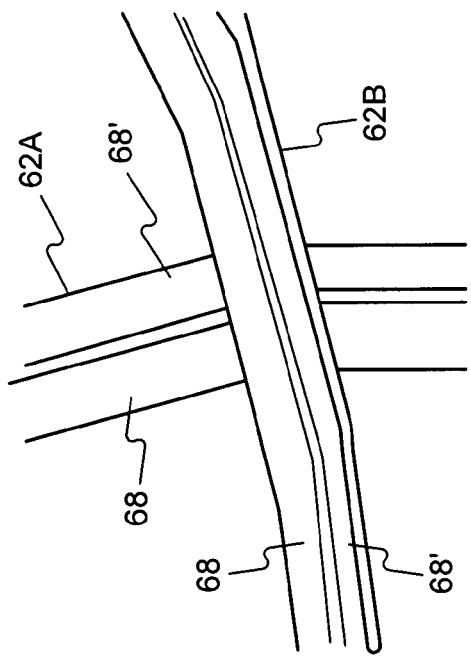
FIG. 9 illustrates an enlarged view of legs of the medical retrieval basket of FIG. 8, according to an embodiment of the invention.
Figure 8:
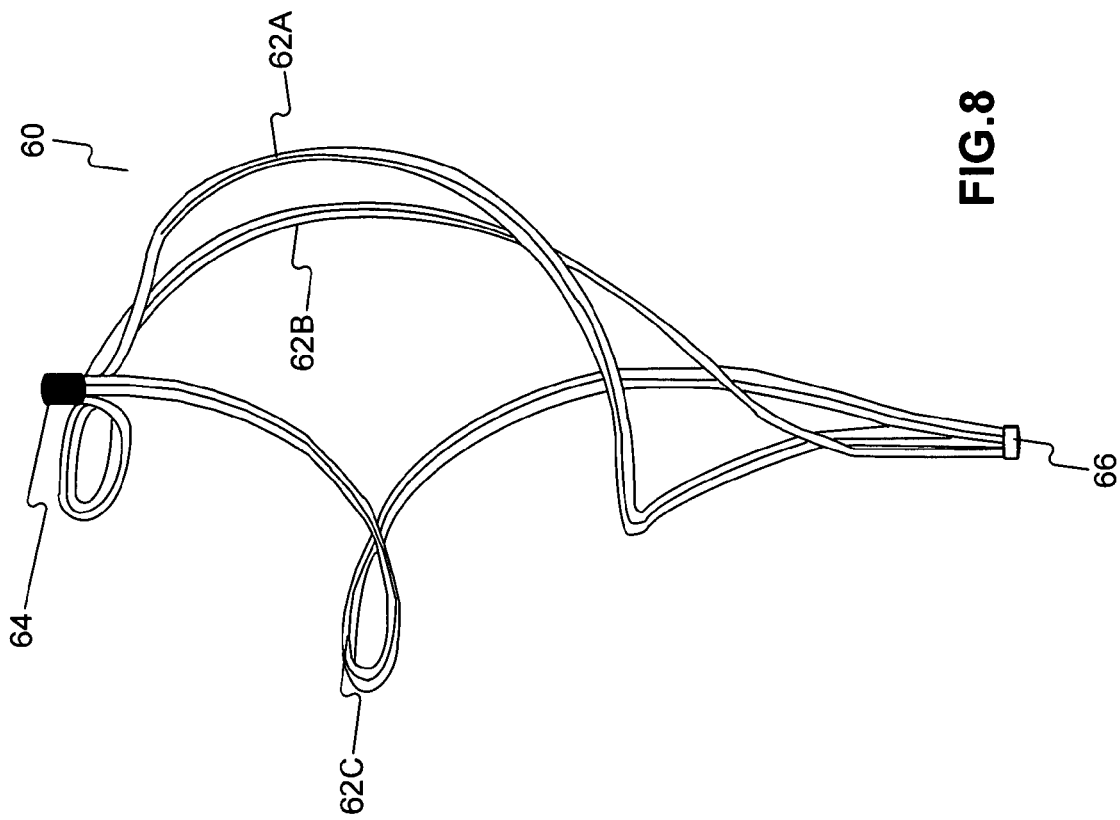
FIG. 8 is a perspective view of a medical retrieval basket depicting a paired leg configuration, according to another embodiment of the present disclosure.

FIG. 8 depicts a perspective view of a medical retrieval basket according to another embodiment of the present disclosure. FIG. 8 depicts medical retrieval basket 60 having a three legged configuration. Basket 60 is comprised of three struts 62A-62C joined together at a distal end 64 and a proximal end 66 of basket 60. The struts 62A-62C twist in a spiral configuration about the longitudinal axis of the basket 60. In addition, each individual strut 62A, 62B, and 62C is formed as a combined unit comprised of a pair of legs. For example, as seen in FIG. 9, each of the illustrated struts 62A and 62B is provided in a reinforced configuration formed by providing a pair of parallel legs 68 and 68' to form the individual struts 62A, 62B.

Legs 68 and 68' of each strut 62 can be arranged to minimize space therebetween. For example, legs 68 and 68' can be formed of a shape memory material so that the legs are configured to exhibit substantially identical complementary shapes and are matched together in a rest position with little or no space between the legs. The legs of a pair can be connected at one or more points along their length. Connection can be effectuated through welds, adhesives, or soldering, for example. Connection can also be made by leaving material along the slots or cuts made in a tube from which the legs are formed. In other words, a discontinuous slot or cut made in a tube will leave adjacent legs connected at the discontinuities.

Figure 13:
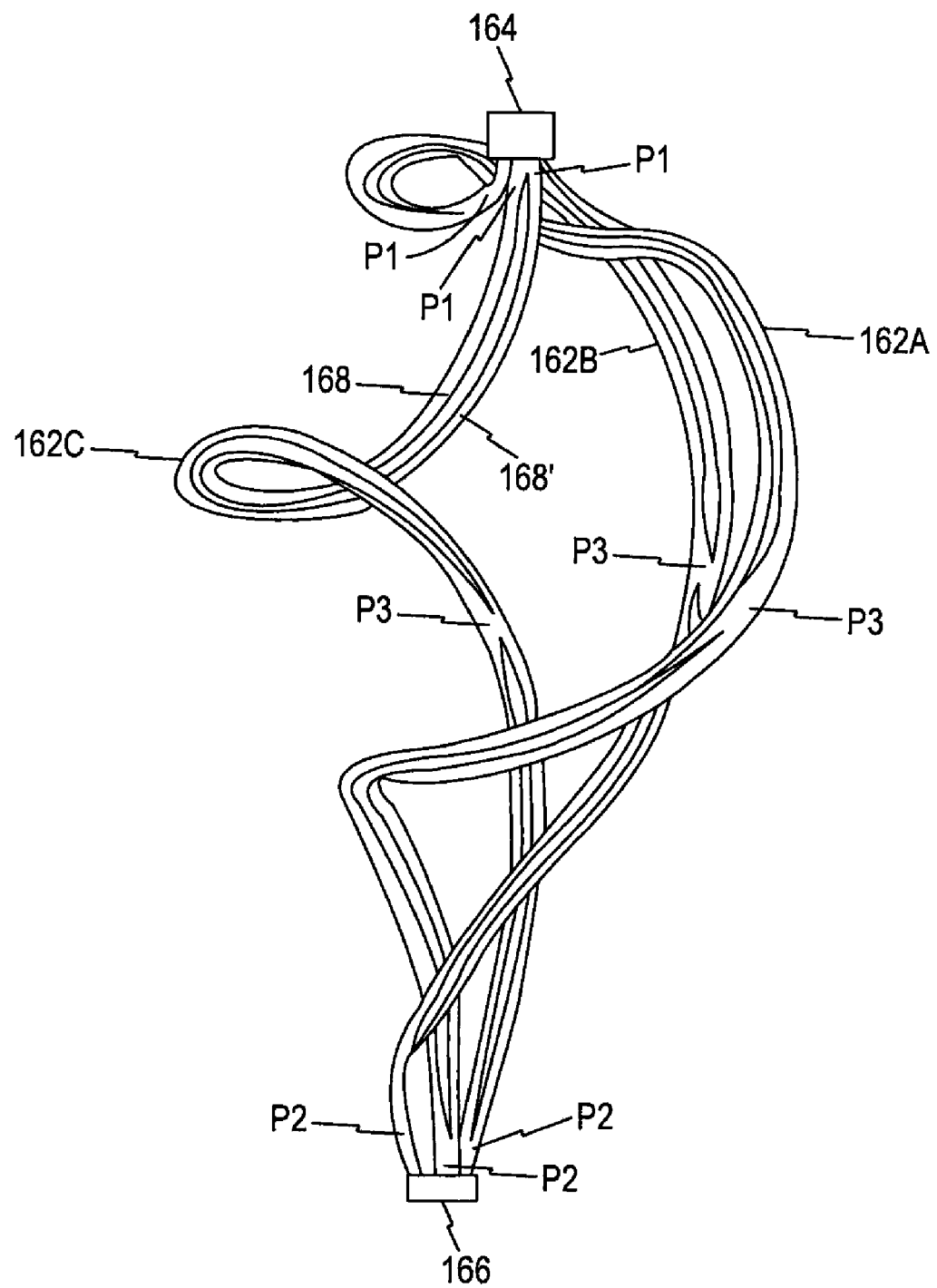
FIG. 13 is a perspective view of a medical retrieval basket depicting a paired leg configuration, according to another embodiment of the present disclosure.

For example, in FIG. 13, legs 168, 168' of struts 162 are permanently connected at multiple points along the longitudinal axis of the basket. The multiple points may include at least a first point P1, a second point P2, and a third point P3. In the embodiment shown in FIG. 13, the third point P3 is located between first point P1 and second point P2 along the longitudinal axis, and the two legs are unconnected between first point P1 and the third point P3 and between second point P2 and third point P3. Alternatively, the legs 68, 68' of a strut 62 can be connected only at the distal end 64 and a proximal end 66 of the basket 60, as depicted in FIG. 8.

The enlarged struts of basket 60 facilitate the retention of captured material, while the spiral shape and small number of struts facilitates the controlled release of material by providing relatively large basket openings between struts. One of the benefits of the paired leg strut is having the flexibility of a single leg with the strength of the added material of the pair of the strut. Accordingly, the embodiment of FIG. 8 represents a compromise between the stone retention benefits of a basket having a relatively large number of legs and the release benefits of a spiral basket. While the embodiment of FIG. 8 is depicted as having three paired-leg struts, alternative arrangements are contemplated, including, but not limited to, four paired-leg struts. In addition, the paired strut arrangement of FIG. 8 can be combined with the merged leg features in the embodiments of FIGS. 3 and 7. For example, four pairs of legs could be formed to merge into two pairs of legs (i.e. four struts into two struts) at an intermediate portion of a basket.

FIG. 10 depicts a perspective view of a medical retrieval basket having a herringbone shaped configuration, according to an embodiment of the present disclosure. An example of a herringbone pattern or shape includes, but is not limited to, a pattern made up of rows of parallel elements, such as, for example, slots, which in any two adjacent rows slope in opposite directions.

FIG. 10 depicts a medical retrieval basket 70 comprised of four legs 72A-72D joined together at a distal end 74 and a proximal end 76 of basket 70. With reference to FIG. 12, basket 70 is formed from a tube 78. Tube 78, depicted in a flattened configuration in FIG. 12, includes four slots 79 extending along the tube 78. The slots 79 are formed in a herringbone pattern exhibiting cuts that extend diagonally in one direction and then slant at an intermediate point to change direction and extend diagonally in another direction. The number of slots 79 can be increased or decreased depending on the number of legs desired for basket 70 of FIG. 10.

Referring again to FIG. 10, the basket 70 resulting from the slot pattern of FIG. 12 exhibits a dual spiral configuration. As seen in FIG. 10, the proximal portion of each of legs 72A-72D twists in a spiral configuration in a clockwise direction, for example, about the longitudinal axis of the basket 70. The distal portion of each of the legs 72A-72D, conversely, twists in a spiral configuration in a counter-clockwise direction. The point along the basket 70 where the spiral configuration shifts from one direction to another depends on the selection of the location where each angled slot 79 changes direction in the slotting pattern for tube 78.

FIG. 11 depicts a top view of the basket 70 of FIG. 10. Since each of legs 72A-72D extends in a spiral in a first direction and at an intermediate point converts to extend in a spiral in a second direction. The top view of FIG. 11 only depicts a partially completed spiral pattern with the reversed spiral pattern of each leg depicted in dashed lines. The resulting configuration of FIGS. 10-12 combines the stone capture ability of a helical basket with the leg spacing benefits of a straight legged basket.

Alternative herringbone basket shapes are also contemplated. For example, the angle formed by the slot 79 can be increased or decreased. In addition, a repeating pattern of angled slots 79 can be formed in tube 78, resulting in a basket configuration exhibiting multiple consecutive alternating spiral patterns (i.e. a clockwise spiral, followed by a counter clockwise spiral, followed by a clockwise spiral, and so forth). Furthermore, the consecutive patterns of such a series could each be slightly altered in one fashion or another to provide a number of alternative configurations. In addition, the herringbone configuration of FIGS. 10-12 can be incorporated with the dual merged leg basket features of FIGS. 3 and 7.

While the forgoing embodiments have been described individually, it is intended that the disclosed features of the various basket arrangements are combinable and interchangeable in any fashion. For example, it is intended that any of the disclosed basket embodiments could be arranged to further include the merged leg feature, the spiral leg feature, the paired leg feature, and the herringbone leg feature, and/or any combination thereof.

In addition, as an alternative to forming a retrieval basket from a tube or cannula as explained in the foregoing portions of this disclosure, the various baskets described herein could also be formed using individual wire strands. Such an approach could duplicate the effect of the long merged leg features by winding the wires of the primary basket legs proximal to the basket. Furthermore, a standard wire arrangement could be shaped and bound into the herringbone design.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   a sheath having a proximal end and a distal end;
   a basket for removing material from a body, the basket having a distal end, a proximal end, a longitudinal axis, a collapsed position where the basket is enclosed within the sheath, and an expanded position where the basket extends from the distal end of the sheath, and
   wherein the basket includes at least two struts each comprised of two legs united in a paired configuration, the struts twisting in a spiral configuration about the longitudinal axis of the basket, and
   wherein the two legs of each strut are permanently connected at multiple points along the longitudinal axis of the basket,
   wherein the multiple points include at least a first point, a second point, and a third point, wherein the third point is located between the first point and the second point along the longitudinal axis, and the two legs are unconnected between the first point and the third point and between the second point and the third point.

2. The medical device of claim 1, wherein the basket includes a distal basket portion and a proximal basket portion, the distal basket portion including at least three struts, and wherein the struts of the distal basket portion merge to form two struts in the proximal basket portion.

3. The medical device of claim 2, wherein each of the two struts of the proximal basket portion is wider than each of the at least three struts of the distal basket portion.

4. The medical device of claim 2, wherein the struts of the distal basket portion merge at a basket point midway between the distal and proximal ends of the basket.

5. The medical device of claim 1, wherein the basket is formed by cuts made in a hollow tube.

6. The medical device of claim 1, wherein the two legs of each strut are comprised of a shape memory material and exhibit substantially identical shapes.

7. The medical device of claim 1, wherein the two legs of each strut are permanently connected through welds, solder, or adhesives.

8. The medical device of claim 1, wherein the legs are comprised of individual metal wires.

9. The medical device of claim 1, wherein the two legs of each strut are permanently connected at multiple points between the distal and proximal ends of the basket, so that the two legs do not separate at the multiple points in all operational states.

10. A medical device, comprising:
a sheath having a proximal end and a distal end;
a basket for removing material from a body, the basket having a distal end, a proximal end, a longitudinal axis, a collapsed position where the basket is enclosed within the sheath, an expanded position where the basket extends from the distal end of the sheath, and at least two struts extending between the distal and proximal basket ends, each of the struts having a first portion extending from the proximal end of the basket and twisting in a first spiral direction around the longitudinal axis, and a second portion extending between the first portion and the distal end of the basket, the second portion twisting in a second spiral direction around the longitudinal axis, the second spiral direction being opposite of the first spiral direction,
wherein the basket includes a distal basket portion and a proximal basket portion, the distal basket portion including at least three struts that merge to form two struts in the proximal basket portion,
wherein each strut is comprised of two legs united in a paired configuration,
wherein the two legs of each strut are permanently connected at multiple points along the longitudinal axis of the basket,
wherein the multiple points include at least a first point, a second point, and a third point, wherein the third point is located between the first point and the second point along the longitudinal axis, and the two legs are unconnected between the first point and the third point and between the second point and the third point.

11. The medical device of claim 10, wherein each of the two struts of the proximal basket portion is wider than each of the at least three struts of the distal basket portion.

12. The medical device of claim 10, wherein the at least three struts of the distal basket portion merge at a basket point midway between the distal and proximal ends of the basket.

13. The medical device of claim 10, wherein the basket is formed through cuts made in a hollow tube.

14. The medical device of claim 10, wherein all the struts are comprised of individual metal wires.

15. The medical device of claim 10, wherein the first portion and the second portion substantially curve around a circumference of the basket as the first portion twists in the first spiral direction and the second portion twists in the second spiral direction.

16. The medical device of claim 10, wherein the first portion and the second portion are not parallel.

17. A medical device, comprising:
a sheath having a proximal end and a distal end;
a basket for removing material from a body, the basket having a distal end, a proximal end, a longitudinal axis, a collapsed position where the basket is enclosed within the sheath, and an expanded position where the basket extends from the distal end of the sheath,
wherein the basket includes at least one strut having a first portion extending from the proximal end of the basket to an intermediate point between the proximal and distal ends of the basket and twisting in a first spiral direction around the longitudinal axis, and a second portion extending distally from the intermediate point and twisting in a second spiral direction around the longitudinal axis, the second spiral direction being opposite of the first spiral direction,
wherein the at least one strut is comprised of two legs united in a paired configuration,
wherein the two legs of the at least one strut are permanently connected at multiple points along the longitudinal axis of the basket,
wherein the multiple points include at least a first point, a second point, and a third point, wherein the third point is located between the first point and the second point along the longitudinal axis, and the two legs are unconnected between the first point and the third point and between the second point and the third point.

18. The medical device of claim 17, wherein the first spiral direction is clockwise and the second spiral direction is counter-clockwise.

19. The medical device of claim 17, wherein the at least one strut includes a third portion twisting in the first spiral direction about the longitudinal axis, the second portion being between the first and third portions.

20. The medical device of claim 17, wherein the at least one strut includes four struts.

21. The medical device of claim 17, wherein the basket includes a distal basket portion and a proximal basket portion, the distal basket portion including at least three struts, and wherein the struts of the distal basket portion merge to form two struts in the proximal basket portion.

22. The medical device of claim 21, wherein each of the two struts of the proximal basket portion is wider than each of the at least three struts of the distal basket portion.

23. The medical device of claim 21, wherein the at least three struts of the distal basket portion merge at a basket point midway between the distal and proximal ends of the basket.

24. The medical device of claim 17, wherein the at least one strut is an individual metal wire.

25. The medical device of claim 17, wherein the basket is formed through cuts made in a hollow tube.

26. The medical device of claim 25, wherein the cuts form a herringbone pattern.

27. The medical device of claim 17, wherein the basket has a substantially asymmetric shape in the expanded position.

28. The medical device of claim 17, wherein the first portion and the second portion substantially curve around a circumference of the basket as the first portion twists in the first spiral direction and the second portion twists in the second spiral direction.

29. The medical device of claim 17, wherein the first portion and the second portion are not parallel.

* * * * *